United States Patent
Arzhakova et al.

(10) Patent No.: US 8,834,795 B2
(45) Date of Patent: Sep. 16, 2014

(54) OPTOCHEMICAL SENSOR FOR SENSING $O_2$, AND METHOD OF ITS PREPARATION

(75) Inventors: Olga Vladimirovna Arzhakova, Moscow (RU); Nikolai Filippovich Bakeev, Moscow (RU); Aleksandr L'vovich Volynskii, Moscow (RU); Alla Anatol'evna Dolgova, Khimki (RU); Larisa Mikhailovna Yarysheva, Moscow (RU); Ponomarev Gelii Vasilievich, Moscow (RU)

(73) Assignee: Luxcel Biosciences Limited, Cork (IE)

( * ) Notice: Subject to any disclaimer, the term of this patent is extended or adjusted under 35 U.S.C. 154(b) by 302 days.

(21) Appl. No.: 13/131,937

(22) PCT Filed: Dec. 11, 2008

(86) PCT No.: PCT/EP2008/010577
§ 371 (c)(1),
(2), (4) Date: May 31, 2011

(87) PCT Pub. No.: WO2010/066273
PCT Pub. Date: Jun. 17, 2010

(65) Prior Publication Data
US 2011/0244592 A1 Oct. 6, 2011

(51) Int. Cl.
*G01N 21/00* (2006.01)
*G01N 31/22* (2006.01)
(Continued)

(52) U.S. Cl.
CPC .............. *G01N 31/225* (2013.01); *G01N 31/22* (2013.01); *G01N 21/78* (2013.01); *B01D 67/0023* (2013.01); *G01N 21/643* (2013.01); *G01N 2021/7786* (2013.01)
USPC ......... 422/82.05; 436/164; 436/165; 436/166

(58) Field of Classification Search
CPC .......... A61K 2800/413; A61K 8/0279; G01N 2021/7786; G01N 21/643; G01N 31/225; G01N 21/78; G01N 31/2221; B01D 67/0023
See application file for complete search history.

(56) References Cited

U.S. PATENT DOCUMENTS

| 3,102,322 | A | 9/1963 | Whitaker |
| 3,233,019 | A | 2/1966 | Adams |

(Continued)

FOREIGN PATENT DOCUMENTS

| EP | 0 091 390 | 10/1983 |
| RU | 2305724 | 9/2007 |

(Continued)

OTHER PUBLICATIONS

Basabe-Desmonds et al. "Design of fluorescent materials for chemical sensing", Chem. Soc. Rev., 2007, v. 36, pp. 993-1017, published on-line Feb. 2, 2007.*

(Continued)

*Primary Examiner* — Yelena G Gakh
(74) *Attorney, Agent, or Firm* — Cesari and McKenna, LLP

(57) ABSTRACT

An optochemical sensor element suitable for sensing an analyte comprises a polymeric material in which at least a portion of the polymer material is solvent crazed to provide a multiplicity of pores of controlled nanometer size, and an indicator dye impregnated into the pores, in which optochemical sensor element the indicator dye is a long-decay photoluminescent dye selected from the group consisting of: phosphorescent platinum(II)—and palladium (II) complexes of porphyrin dyes such as octaethylporphine, coproporphyrin, octaethylporphine-ketone, benzoporphine, tetra (pentafluorophenyl) porphine, chlorin e6; fluorescent complexes of ruthenium (II), osmium(II), iridium(III) and europium (III); or derivatives or close analogs of these dyes. The sensor element in the presence of the analyte alters a photoluminescence parameter thus allowing sensing and/or quantification of the analyte.

10 Claims, 3 Drawing Sheets

(51) Int. Cl.
*G01N 21/78* (2006.01)
*B01D 67/00* (2006.01)
*G01N 21/64* (2006.01)
*G01N 21/77* (2006.01)

(56) References Cited

U.S. PATENT DOCUMENTS

| | | | |
|---|---|---|---|
| 4,001,367 | A | 1/1977 | Guthrie et al. |
| 4,003,707 | A | 1/1977 | Lubbers et al. |
| 4,055,702 | A | 10/1977 | Guthrie et al. |
| 4,810,655 | A | 3/1989 | Khalil et al. |
| 5,030,420 | A | 7/1991 | Bacon et al. |
| 5,222,092 | A * | 6/1993 | Hench et al. ............ 372/53 |
| 5,407,829 | A * | 4/1995 | Wolfbeis et al. ............ 436/1 |
| 5,718,842 | A | 2/1998 | Papkovsky et al. |
| 5,837,865 | A | 11/1998 | Vinogradov et al. |
| 6,653,148 | B2 | 11/2003 | Trapp et al. |
| 6,815,211 | B1 | 11/2004 | Blazewicz |
| 2006/0257094 | A1 | 11/2006 | McEvoy et al. |
| 2007/0243618 | A1 | 10/2007 | Hatchett |
| 2008/0286154 | A1 | 11/2008 | Kane |

FOREIGN PATENT DOCUMENTS

| | | |
|---|---|---|
| WO | WO02103334 | 12/2002 |
| WO | WO2008012785 | 1/2008 |

OTHER PUBLICATIONS

Parkovsky, "Method in Optical Oxygen Sensing: Protocols and Critical Analyses", Methods in Enzymology, 2004, vol. 381, pp. 715-735.*

Parkovsky et al., "Biosensors on the basis of luminescent oxygen sensor: the use of microporous light-scattering support materials", Elsevier Science S.A., 1998, vol. 51, pp. 137-145.*

Borisov et al., "Poly(styrene-block-vinylpyrrolidone) Beads as a Versatile Material for Simple Fabrication of Optical Nanosensors", Anal. Chem., 2008, vol. 80, No. 3, pp. 573-582.*

Fernandez-Sanchez et al. "Novel nanostructured materials to develop oxygen-sensitive films for optical sensors", Analytica Chimica Acta, 2006, v. 566, pp. 271-282.*

Jeronimo et al. "Optical sensors and 16-25 biosensors based'on sol-gel films", Talanta, 2007, vol. 72, No. 1, pp. 13-27.*

Kumari and Sahare, "Optical Studies of Fluorescent Mesoporous Silica Nanoparticles", J. Mater. Sci. Technol., 2013, v. 29, No. 8, pp. 742-746.*

Papkovsky, Dmitri B., et al., "Phosphorescent Sensor Approach for Non-Destructive Measurement of Oxygen in Packaged Foods: Optimisation of disposable Oxygen Sensors and Their Characterization Over a Wide Temperature Range", Analytical Letters, vol. 33(9), pp. 1755-1777 (2000).

Volynskii, A.L., "Structure and Properties of Low-Molecular-Mass Substances in Solvent-Crazed Polymer Matrices", Polymer Science, vol. 44, No. 1, 2002, pp. 83-99.

* cited by examiner

OPTOCHEMICAL SENSOR FOR SENSING $O_2$, AND METHOD OF ITS PREPARATION

RELATED APPLICATIONS

This application is the national stage application under 35 USC 371 of PCT/EP2008/010577, filed on Dec. 11, 2008, the contents of which are herein incorporated by reference.

FIELD OF THE INVENTION

The invention relates to material chemistry, sensors, (bio) analytical and detection systems, particularly to indicator-mediated sensors based on optical detection. The invention can be used in biotechnology, chemical and electronic industry, environmental and biomedical applications, process control, packaging of foods, biopharmaceuticals, electronic components and in other areas where measurement of molecular oxygen ($O_2$) and other physical and chemical parameters is required.

BACKGROUND OF THE INVENTION

Over the past decades numerous optochemical sensors and biosensors have been developed for the measurement and continuous monitoring of important physical, chemical and biological parameters. Corresponding sensing materials often rely on indicator dyes incorporated in polymeric matrices, which provide means for qualitative or quantitative assessment of analyte(s) of interest by measuring sensor optical properties. Such materials are routinely used for sensing of: gaseous specie such as oxygen, carbon dioxide, ammonia, sulfur dioxide, organic vapors; ionic specie such as pH, $Na^+$, $K^+$, $Ca^{2+}$, $NH_4^+$, $NO_3^-$, $NO_2^-$, organic molecules and metabolites; other bio- and macromolecules, in conjunction with absorbance, reflectance, fluorescence/phosphorescence, or chemiluminescence detection in the UV-VIS range. Polymeric sensors are commonly used, especially for gaseous analytes and small molecules (e.g. ions) (O. S. Wolfbeis (ed.), Fiber Optic Chemical Sensors and Biosensors, CRC Press, Boca Raton, Fla., 1991, v.1,2). This methodology allows production of sensor elements on both small and large scale using rather simple procedures and equipment.

Molecular oxygen (O2) is the analyte of major importance, and optical oxygen sensors have been investigated for many years. O2 is a quencher of long-decay fluorescent and phosphorescent dyes, so it can be 'sensed' directly by luminescence quenching (Papkovsky D. B., Methods in optical oxygen sensing: protocols and critical analyses, In: Methods Enzymol. 2004, v.383, p. 715-734). For such $O_2$-sensitive materials, both luminescence intensity and decay time of the dye are reduced in the presence of $O_2$, thus allowing quantification, by intensity or lifetime measurements or by phase-fluorometry. Lifetime based sensing of $O_2$ realised by the latter two methods is advantageous for many applications.

O2 sensors are usually prepared in the form of a solid-state material (coating, film, membrane—see e.g. U.S. Pat. Nos. 4,003,707 and 5,718,842), a soluble reagent (probe—see e.g. U.S. Pat. No. 5,837,865 and WO2008012785-A2), a dispersed matter (nano- and micro-particles dopped with indicator dye—see e.g. Borisov, S M, Mayr, T, Klimant, I—Anal Chem, 2008, v.80, p. 573-582), or combinations thereof (e.g. WO2002103334 Klimant I, Krause C). The solid-state sensor approach allows easy manipulation and reuse of sensors, and avoids sample contamination.

To produce a solid-state active element, an $O_2$-sensitive dye is usually embedded in a suitable matrix which provides the desired quenchability and response characteristics (sensitivity, response time, etc.). By selecting the dye, the medium and encapsulation process, one can optimise photophyscial and sensing characteristics for accurate measurement of $O_2$ concentration. Examples of $O_2$-sensitive materials are: pyrene butyrate in silicone rubber (U.S. Pat. No. 4,003,707), Ru-tris(bipirydyl) dye in silicone rubber (U.S. Pat. No. 5,030,420), Ru(dpp)3 dye incorporated in sol-gel matrix—ormosil (US 20060257094; Klimant), Pt-octaethylporphin-ketone dye in polystyrene (U.S. Pat. No. 5,718,842), Pt-tetrakis-(pentafluorophenyl)porphine in a polymer (U.S. Pat. No. 4,810,655 and U.S. Pat. No. 6,653,148).

Fabrication procedures for such sensors usually involve preparation of sensor components in an appropriate solvent (i.e. 'coating cocktail') which is applied on a suitable solid support. After drying, polymerisation or curing, solid-state polymeric composite is formed. Preparation of such thin film O2-sensitive coatings may be achieved by casting, spin-coating, dip-coating, tampon or jet printing, co-polymerization, of such cocktails. Such thin film coatings usually require a special support material to maintain their integrity and stability during operation and handling. However, the need for sensor support leads to a problem of adhesion of sensor composite to it. Strong interaction between the two materials is not desirable as this may lead to the formation of mixed phases and/or regions of heterogeneity, thus affecting sensing properties. Common matrices used in $O_2$ sensors (hydrophobic polymers such as polystyrene) are not very compatible with support materials such as glass or other polymers (e.g. polyethylene and polypropylene widely used in packaging). The use of microporous support materials coated with the polymeric O2-sensitive compositions has been described (Papkovsky D. B. et al. Sens. Actuat. Part B., 1998, v.51, N1-3, p. 137-145). Sensors are prepared in the form of membranes, sheets, inserts, coated fibres, sensor arrays (e.g. coated microplates).

Therefore, fabrication of traditional $O_2$ sensors generally requires the following components: indicator dye, encapsulation medium, support material and solvent. Some additives required for sensor operation (plasticiser) can also be incorporated. The use of such complex cocktails containing polymer and volatile solvents complicates production of sensors and imposes certain restrictions. Thus, viscous and volatile formulations are difficult to handle, manipulate and dispense in small volumes, they tend to dry during casting procedure or printing. Also thin film coatings are fragile, tend to degrade with time, delaminate and fall off, especially from hydrophobic and flexible support materials. Although traditional sensor design and fabrication techniques produce satisfactory sensors, they are relatively complex from the fabrication point of view and not very suitable for certain applications where high accuracy and reproducibility of measurements is required (e.g. with disposable or calibration free sensors). Complex composition and fabrication of the current $O_2$ sensors, non-optimal physical-chemical and sensing properties, limited applicability and analytical performance and relatively high production costs limit their use. Incorporation of such sensors in sample vessels or packages made of inert materials is also difficult and requires additional steps and components (e.g. adhesive). The development of more simple, robust and materials having superior sensing properties is therefore highly needed.

The invention addresses at least one of these issues by providing new materials and fabrication processes which enable advanced sensing systems, and also uses of such sensors in a number of high-utility applications such as packaging, biopharmaceutical, biomedical. It also demonstrates that this approach is applicable to a range of different sensing systems and materials, primarily to fluorescence/phosphorescence based sensors for $O_2$, enzyme biosensors on their basis, but also to other indicator-mediated sensors for pH, $CO_2$ and some other important analytes.

SUMMARY OF THE INVENTION

According to the invention, there is provided an optochemical sensor element suitable for sensing an analyte comprising a solvent crazed polymeric material (i.e. a polymeric material in which at least a portion of the polymer material is solvent crazed) having a multiplicity of pores of controlled nanometer size, and an indicator dye impregnated into the pores, in which the indicator dye is a long-decay photoluminescent dye. The long-decay photoluminescent indicator dye is selected from the group consisting of: phosphorescent platinum(II)- and palladium(II) complexes of porphyrin dyes (such as, for example, octaethylporphine, coproporphyrin, octaethylporphine-ketone, benzoporphine, tetra (pentafluorophenyl)porphine, chlorin e6); fluorescent complexes of ruthenium(II), osmium(II), iridium(III) and europium(III); or derivatives or close analogs of these dyes; wherein the sensor element, in the presence of the analyte, alters a photoluminescence parameter thus allowing sensing and/or quantification of the analyte Typically, the optochemical sensor element is an elongated form such as for example in a form of a sheet, film, tape, strip or fibre. Suitably, the optochemical sensor element has a thickness in the region of from 5 to 500 microns, typically between 5 and 100 microns, preferably between 5 and 50 microns, and ideally between 10 and 40 microns.

Preferably, the solvent crazed portions of the optochemical sensor element have an average pore size of less than 50 nm, and suitably a volume porosity of from 1 to 60%.

In a preferred embodiment of the invention, the pores of the polymeric material impregnated with photoluminescent indicator dye are healed. Suitably, the pores are healed by drying the solvent crazed polymeric material and, optionally, further stretching or heat treatment of the relaxed polymeric material. Other methods of healing the pores will be apparent to the skilled person, including heating, drying, further solvent crazing, radiation treatment, or drawing of the polymeric material, which may be carried out individually or in any combination.

The polymeric material and the indicator dye are selected such that the analyte is capable of accessing the nanopores to interact with the indicator dye.

In a preferred embodiment of the invention, the photoluminescent indicator dye is an $O_2$ sensitive dye, and wherein the polymeric material has moderate permeability to $O_2$. Typically, the polymeric material is selected from the group consisting of: high density polyethylene (HDPE); polypropylene; polyolefins; and halogenated polyolefin. Other polymeric materials having moderate permeability to $O_2$ in the context of the invention will be known to the skilled person. Numerous examples of $O_2$ Sensitive dyes are disclosed herein.

In one embodiment of the invention, the indicator dye comprises a photoluminescent pH-sensitive dye and the polymeric material comprises HDPE.

In one embodiment of the invention, the indicator dye comprises a photoluminescent temperature-sensitive dye and the polymeric material comprises PVC.

The invention also relates to a system for detecting an analyte comprising an optochemical sensor element of the invention operatively connected to a detector capable of detecting photoluminescence emitted by the optochemical sensor element.

Suitably, the detector is specifically adapted to detect a parameter of photoluminescence selected form the group consisting of: intensity; lifetime; and phase shift signal; or a combination thereof.

The invention also relates to a packaged product comprising: packaging; a product contained within the packaging; and an optochemical sensor element of the invention disposed within the packaging and adapted to detect an analyte (or a change in environment) within the packaging.

Typically, the analyte (or the change in environment) is selected from the group consisting of: change in residual oxygen, change in temperature; change in pH.

Suitably, the product is selected from the group consisting of: a solid, semisolid, or liquid foodstuff; a pharmaceutical; and an electronic product.

Preferably, the sensor element is heat-sealed to an internal face of the packaging material.

The invention also provides a process for producing an optochemical sensor element suitable for sensing an analyte comprising the steps of:
    providing a polymeric material at least a portion of which is solvent crazed to provide a multiplicity of pores of controlled nanometer size; and
    impregnating the pores with an indicator dye selected from the group consisting of long-decay photoluminescent dyes which show sensitivity to the analyte,
wherein the polymeric material, the indicator dye, and the impregnation step are selected such that the resulting optochemical sensor element shows a characteristic optical response to the analyte by altering the parameters of its photoluminescence.

Typically, the process includes a step of solvent-crazing an amorphous or semi-crystalline polymeric material to provide the multiplicity of pores of controlled nanometric size.

In a preferred embodiment, the solvent-crazing step and impregnation step are carried out in a single step, wherein the long-decay photoluminescent indicator dye is incorporated into the solvent employed in the solvent-crazing step.

Suitably, the solvent crazing step comprises drawing the polymer by a factor of at least 1%, preferably at least 2%, 3%, 4% and 5%.

Typically, the process of the invention includes a further step of healing the pores of the polymeric material impregnated with photoluminescent indicator dye.

In one embodiment, the healing step comprises drying the solvent crazed polymeric material and, optionally, further stretching or heat treatment of the relaxed polymeric material.

Suitably, the polymeric matrix, the photoluminescent indicator dye, the solvent crazing, impregnation and healing steps are selected such that the resultant optochemical sensor element provides a desired sensitivity and selectivity for the analyte.

Typically, the process involves use of a polymeric material having an elongated form and, ideally, a thickness of from 5 to 500 microns, typically between 5 and 100 microns, preferably between 5 and 50 microns, and ideally between 10 and 40 microns.

A polymeric material at least a portion of which is solvent crazed to provide a multiplicity of pores of controlled nanometer size, and a photoluminescent indicator dye impregnated into the pores, and wherein the polymeric material and indicator dye are selected such that, when incorporated into the nanopores, the indicator dye is responsive to an external parameter selected from the group consisting of: O2; temperature; and pH.

A method of sensing an analyte comprising a step of exposing an optochemical sensor element of the invention to an environment in which the analyte is to be detected, and detecting a characteristics optical response of the sensor element to the analyte.

DETAILED DESCRIPTION OF THE INVENTION

Figure 1:
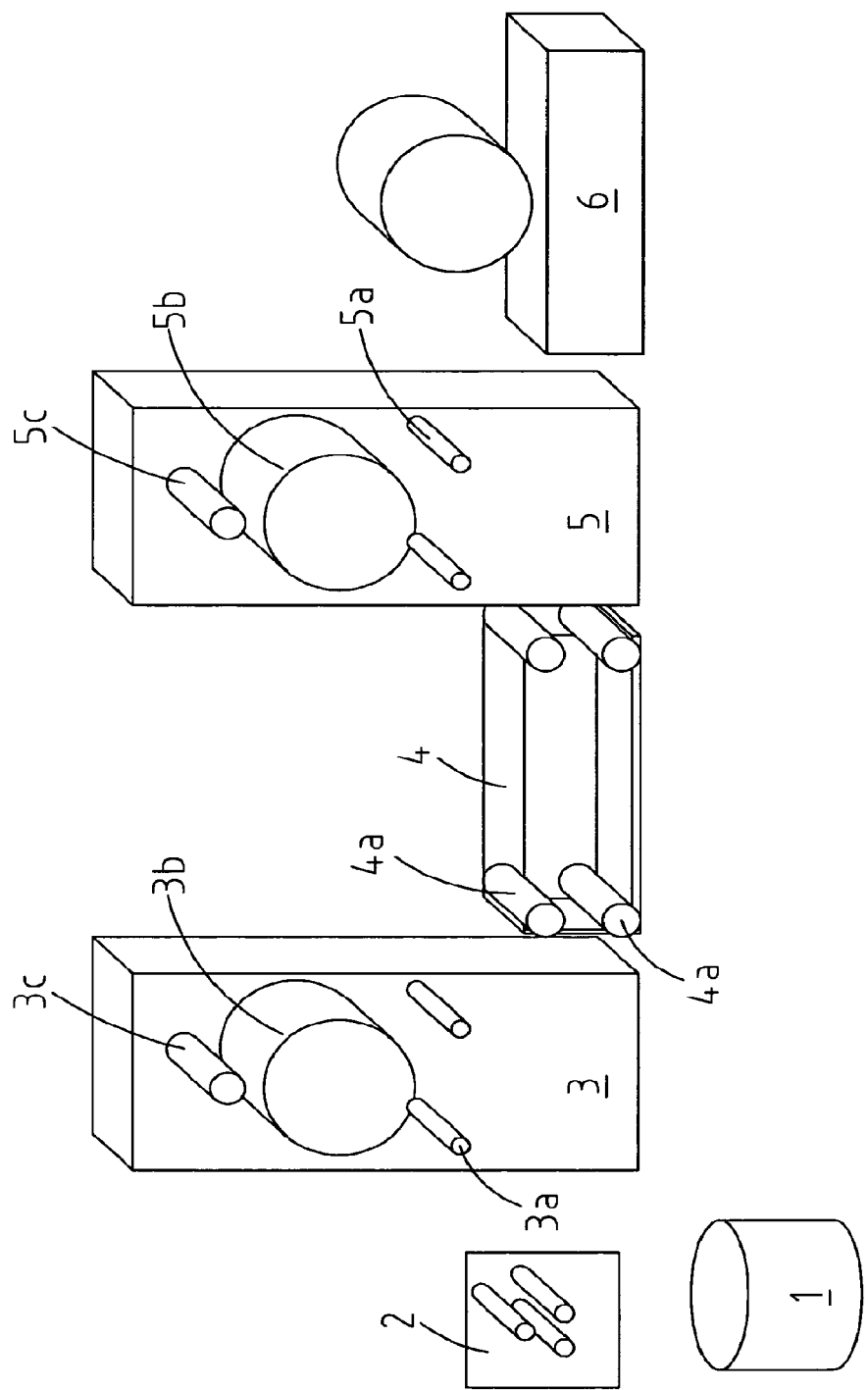
FIG. 1. illustrates a system for solvent crazing a polymer.

The invention provides a range of new, advanced materials for optical sensing of important chemical and biological species and parameters. It also provides special techniques for the fabrication of such sensors and methods of their use in a number of important applications. The invention is particularly focused on the sensors for molecular oxygen ($O_2$) which are based on the phenomenon of quenching of fluorescence or phosphorescence. At the same time, it is applicable to many other indicator-mediated sensor systems.

According to the invention, sensor active elements are produced using special nanostructured polymeric materials which are impregnated with indicator dyes according to procedures specially developed and optimised for these purposes. One of the key aspects of the invention is the use of solvent-crazed polymers for sensor design and fabrication. The process of solvent- or wet-crazing of polymers is known for some time (see e.g. Volynskii et al., Polymer Science, 2002, v. 44, p. 1701; Russian Patent 2305724, 2006) and has been used for staining polymers with various substances. However, these materials and processes have not been explored or used in optochemical sensors, particularly sensors for gaseous analytes such as $O_2$. In this invention it is demonstrated that such sensor technology and materials possess a number of useful features which were not known from prior art. Thus, compared to the existing sensors, the new materials display many advantages that allow simple fabrication procedures, fine-tuning of sensor working characteristics and interfacing with the sample and light detector. The invention enables the implementation in such sensors of a number of important specifications, which have been difficult to implement with existing sensor technologies. It also provides a basis for a family of enzyme biosensors in which these nanostructured materials are used as optical transducers.

Design and fabrication of the sensors of the invention generally involves the following main steps: i) selection of the indicator dye and polymeric material for a given sensing application; ii) optionally, treatment of the polymer by solvent crazing process; iii) impregnation of solvent-crazed polymeric structure with indicator dye molecules (and with other components, if required); iv) optionally, post-treatment of impregnated nanostructured polymers. In different embodiments of the invention, some of these steps may be combined, for example, crazing and impregnation; crazing, impregnation and post-treatment. Some steps can be omitted, for example post-treatment, or added, such as additional impregnation or coating with an enzyme. After fabrication, such sensors are incorporated in test samples and/or interfaced with the detector to allow analyte quantification. These aspects of sensor technology are also addressed in the invention.

Selection of the polymer and indicator dye for sensor fabrication is based on a number of criteria. For example, for $O_2$ sensors the indicator dye should have one or more of convenient photophysical properties (excitation and emission wavelengths, photostability), optimal quenchability by $O_2$ (moderate for measurement in the physiological range 0-21 kPa $O_2$ and high for trace $O_2$ detection), relatively long emission lifetimes (to facilitate lifetime based sensing), low intrinsic toxicity (e.g. for food or medical applications), be affordable and compatible with the polymer and processes used. Many of the $O_2$-sensitive dyes used in conventional $O_2$ sensors satisfy these requirements. Selection of the polymer for O2 sensors is based on factors such as permeability, diffusion coefficients and solubility for $O_2$ (these determine accessibility and quenchability of the dye and response time), optical properties (clear, opaque, non-transparent), physical-chemical and mechanical properties (robustness, ease of handling, manipulation), compatibility with the sample (food, alcohol, organic solvents), inertness, safety and price. Conventional polymeric materials in the form of a film, tape, sheet, fiber or other polymeric article of elongated shape are preferred for the invention. However, as shown below, selection process differs significantly from that used in traditional sensor technology.

Selected polymeric materials undergo the process of solvent or wet crazing which involves tensile drawing of the polymer in at least one direction in the presence of crazing-promoting wetting liquid. Such straining of the polymeric article which usually has elongated shape (e.g. sheet, tape, film, fibre or other elongated article) is normally conducted in a common organic solvent such as heptane, hexane, isopropanol, other alcohols or alcohol-water mixtures, for example as described e.g. in Adams U.S. Pat. Nos. 3,233,019 and 3,102,323; Guthrie U.S. Pat. Nos. 4,001,367 and 4,055,702. These manipulations produce a derived polymeric material, which has nanometer pores of controlled size and high volume porosity. The solvent-crazing process is applicable to many synthetic organic polymers which are mass-produced for various industrial applications including packaging. Examples include industrial plastics such as high density polyethylene (HDPE), polypropylene (PP), polyolefins, polyvinylchloride; synthetic linear polyesters, such as poly (ethylene terephthalate), often referred to as a homopolymer, or 2G-T; copolyesters, polyamides, e.g., nylon 66, nylon 6, and copolyamides, polyalkylenes; and some other polymers and co-polymers.

Such nanostructured polymers produced by solvent-crazing process can then be impregnated with indicator dyes. Various compounds, which can be dissolved, dispersed or emulsified in a suitable liquid or vaporised solvent and which generally have a maximum particle size less than 50 nm, can be used for the impregnation. For example, incorporation of the $O_2$-sensitive dye can be done by stretching the polymer in the presence of a crazing solvent containing the dye dissolved in it. In this case, the solvent and dye molecules go into the pores when they are formed, filling the microvoid network formed during the solvent crazing process. Alternatively, dye molecules can be loaded to a pre-formed solvent-crazed polymeric structure, wherein the microvoids containing the drawing medium are already formed. In this case, the compounds diffuse into the microvoids and displace a portion of the drawing medium. During subsequent drying or stretching, small solvent molecules leave the pores, while larger, non-volatile dye molecules are retained and stuck inside the pores. Such process provides efficient loading of different dyes and permanent impregnation of such polymers.

It is shown herein that a number of common industrial polymers produced in bulk quantities and in different forms and shapes, particularly amorphous and semi-crystalline polymers such as HDPE, PP and some other polymers and co-polymers, are well suited for the fabrication of sensors of the invention, particularly the $O_2$ sensors. Prior to the invention some of these polymers had limited use in sensors, as they are difficult to dissolve and use in coating cocktails. Solvent-crazing processes provide a simple means for efficient and uniform impregnation of these polymers with various indicator dyes, thus overcoming the issues of chemical compatibility/solubility of the dye and the polymer matrix.

The steps of solvent-crazing of polymeric articles and their impregnation with indicator dyes to produce sensors may be implemented as a multi-step batch process. This process includes, for example, stretching of the polymer in a crazing solvent, then drying the solvent, applying a solution of the dye in the same or different solvent, washing (to remove excess of the dye outside the pores) and drying of impregnated polymer. Alternatively, fabrication procedure can be combined in one continuous process, in which a polymer film, sheet or tape is passed through a reservoir with crazing-promoting solvent containing dissolved dye. The polymer is stretched in this solvent reservoir (e.g. using sets of rolls rotating at different speed), so that it forms the desired nanostructure and takes up the dye from bathing solution. More details of these fabrication and impregnation processes are provided below.

The technique of solvent crazing also provides flexibility in fabricating sensors of different type. In particular, it may be applied to defined zones of a polymeric article leaving the rest of it unmodified (i.e. without characteristic nanoporous structure). This can be achieved, for example, with a special tool that applies pressure to particular regions of a polymer article stretching them in a crazing-promoting solvent and producing nanoporous structures with pre-defined characteristics. If such article is then exposed to a solution of dye, only solvent-crazed zones undergo impregnation while the rest of the polymer remains unstained. This allows production of sensor spots in defined locations, for example on a packaging film for a specific product. Alternatively, solvent crazing may be applied to the whole polymeric article producing uniform impregnation, e.g. a tape or sheet which can then be cut into individual sensors. By applying precise volumes of dye solution to the surface of solvent-crazed polymeric article, impregnation of one side or specific regions of the polymeric article can be achieved. This is particularly useful when direct exposure of the sensor to the sample is undesirable (e.g. in packaging application).

A further advantage of sensors based on solvent-crazed polymers, is the possibility of their subsequent controlled modification. Sensor post-treatment allows control of indicator dye microenvironment, location and physical state, giving means to fine-tune sensor working performance. For example, stretching or heat-treatment of the polymeric solvent-crazed sensors may be used to heal the pores and remove the nanoporous structure. Another method is treatment of polymeric articles (dry or wet) with hot vapor or radiation also leading to sample contraction and healing of the nanopores. Post-treatment may be conducted by drying the drawn polymer in free state at room or slightly elevated temperatures; by annealing in free state for the required time periods at temperatures ranging from room temperature to temperatures below glass transition temperature for amorphous glassy polymers, or below melting temperature for semi-crystalline polymers; by post-stretching at least in one directions by strains varying from 5 to 300%; by annealing of wet free-standing samples at temperatures below glass transition temperature for amorphous glassy polymers or below melting temperatures for semi-crystalline polymers. This is described in more detail below. By applying the post-treatment further improvements and protection of the dye from sample components while retaining access for the analyte can be achieved.

A number of particular sensor types based on solvent-crazed polymers and procedures for their fabrication were developed and optimised in this invention. The resulting sensors display a number of advantages over the existing sensors of similar type, and they enable to match some difficult application requirements. With the following examples of nanoporous $O_2$ sensors and some other (bio)sensors, particular details of their design, fabrication processes, characteristic features and specific applications are demonstrated.

The main requirements for polymeric materials for $O_2$ sensors of the invention typically include the following. The polymer has to be compatible with the solvent-crazing and impregnation processes; be relatively permeable to $O_2$; have the desired mechanical and physical-chemical characteristics and operational stability. The polymers suitable for the fabrication of solvent-crazed $O_2$ sensors may be clear, opaque or white (scattering), whereas highly coloured/dark, mechanically unstable or fragile polymers and polymers containing additives that may leak or evaporate with time (e.g. plasticizers) are sometimes undesirable. Heat-sealing capabilities is also advantageous for some applications. In this invention, a range of nanoporous $O_2$ sensors are produced from several common polymers and $O_2$-sensitive dyes. Different solvent-crazing, impregnation and post-treatment procedures are applied to optimise sensor working characteristics. The preferred shape of the polymer for sensor fabrication is a film, sheet, tape or some other elongated article having thickness in the region of 5-500 microns. HDPE and PP were found to be particularly suitable matrices for $O_2$ sensors.

Using solvent-crazed polymers with highly dispersed nanoporous structure and impregnation by imbibition, drawing or other means, favorable incorporation of O2-sensitive dye molecules and uniform distribution within the polymer can be achieved. For such sensors optical signals were seen to be high and comparable with traditional sensors. Furthermore, sensor calibrations showed good linearity in Stern-Volmer plots, thus reflecting high degree of homogeneity of the dye within the polymer. In contrast, traditional $O_2$ sensors based on thin film coatings usually display marked heterogeneity and complex calibrations, which is linked to the heterogeneous nature of bulk polymers and mechanical stress they undergo during sensor fabrication (large volume reduction during solvent evaporation). The nanostructured polymers of the invention having high volume porosity are easily permeable to gaseous analytes such as $O_2$. Therefore, relatively thick sensor films (up to ~500 microns) can be used which provide good mechanical strength, easy handling and robustness, while still retaining fast response time. Large volume porosity of the nanostructured polymers also provides high loading capacity for the dye.

In one embodiment, sheets of HDPE film (10-100 microns thick) underwent crazing in hexane and impregnation with Pt(II)-octaethylporphine-ketone (PtOEPK) and PdOEPK (U.S. Pat. No. 5,718,842) by spotting dye solution in ethylacetate (1 mg/ml) of the surface of solvent-crazed polymers.

After solvent evaporation and rinsing with solvent, staining of the polymer composite was retained and it showed bright phosphorescence and sensitivity to $O_2$ in the surrounding medium. The properties of such sensors resembled those of the traditional PtOEPK-polystyrene based sensors, but at the same time they displayed a number of unexpected, new features, which are beneficial for practical use. In contrast, when a non-crazed HDPE film was treated similarly with the dye, the dye remained on the surface and aggregated, and resulting materials showed negligible phosphorescence and no sensitivity to $O_2$.

Spectroscopic studies of the solvent-crazed HDPE sensors revealed that PtOEPK dye is trapped and retained inside the polymer matrix, in relatively large amounts and in its monomeric form. The nanoporous structure was seen to restrict the aggregation and self-quenching of the dye, so that it produced bright emission. The polymer also allowed easy access of $O_2$ which effectively quenched the phosphorescence.

Furthermore, quenchability of the dye by $O_2$ in solvent-crazed polymers appeared to be significantly higher than that predicted from the diffusion characteristics of bulk polymers (see e.g. Yasuda H, Stannett V. 1999. Permeability coefficients. In: Polymer handbook, Ed. Bandrup J, 4th edition. New York: Wiley. p 111-229). Despite the fact that diffusion coefficient of $O_2$ in polypropylene is lower than in polystyrene ($9*10^{-8}$ and $1.1*10^{-7}$ cm$^2$/s for bulk polymers, respectively), solvent-crazed PP sensors displayed higher quenching efficiency than polystyrene based sensors prepared by traditional method. Higher sensitivity to $O_2$ facilitates the detection of low levels of $O_2$. In packaging applications sensors of invention provided more sensitive detection of minor leaks of $O_2$ into the sample and breakage of package integrity.

Other $O_2$-sensitive dyes, including Pt(II) and Pd(II) complexes of tetrakis(pentafluorophenyl)porphine, octaethylporphine, tetraphenylporphine, benzoporphyrin, were also incorporated in solvent-crazed polymeric structures, their sensing behaviour was in agreement with expectations and similar to PtOEPK. These $O_2$-sensitive dyes, as well as long-decay fluorescent complexes of transition metals such as Ru(II)polypyridyl, cyclometalated iridium(III), and osmium (II) complexes, their derivatives of close analogs, are preferred indicator dyes for the invention.

As opposed to the traditional $O_2$ sensors, sensors of the invention consist of just two components: the $O_2$-sensitive dye and the polymer (specially treated for the impregnation of the dye and acting as sensor support). Such simple design allows fabrication procedure in which a solution of the dye in organic solvent is simply used as a bathing solution, sprayed, pipetted or printed on the polymer film and then allowed to dry. This process is easy to implement on both small and large scale, in continuous or batch mode with high degree of automation, convenience and productivity. The solvent-crazing process of sensor fabrication allows the use of common polymer materials such as HDPE and PP, which provide good mechanical properties, chemical resistance, inertness, easy handling and incorporation in test samples (packages or food packs), for example by heat-sealing.

Furthermore, application of post-treatment to solvent-crazed $O_2$ sensors (such as the PtOEPK-HDPE sensors), was seen to improve their working characteristics. For these sensors, optimised procedures for modification of solvent-crazed matrix after its impregnation with the dye have been developed which include stretching to desired tensile strains or thermal treatment which provides contraction of the samples (e.g. thermal treatment of dry and wet solvent-crazed samples in fixed or free-stranding state). The preferred post-treatments of the invention are generally mechanical and/or temperature treatments which heal the nanoporous structures and typically restore the normal structure of bulk polymer within the sensor. Such treatment 'zips' the dye in its monomeric form inside the polymer, so that the dye becomes shielded from sample components, protected from leaching and aggregation, while still remains uniformly distributed within the polymer matrix. Compared to the untreated sensors, heat-treated PtOEPK-HDPE sensors produced higher intensity signals and unquenched lifetimes (close to those observed in polystyrene film sensors), and higher sensitivity to $O_2$. Thus, post-treatment of solvent-crazed sensors can be used to fine-tune their properties and sensitivity to $O_2$ in a predictable and reproducible manner.

In contrast, conventional sensors do not show all these features, and therefore they had limited use in many applications where such properties are required. Traditional fabrication techniques (e.g. when the dye and polymer are dissolved in organic solvent and then casted on solid support to produce thin film coatings), appear to be problematic for the above polymers and for some other dye/polymer combinations. For example, insolubility of the polymer in 'friendly' solvents, the lack of solubility of the dye in the polymer or the need of high temperature to melt the polymer for some systems, etc., make the production of cheap and reproducible sensors in large batches difficult, if at all possible. As we demonstrate with HDPE, PP, the invention enables production of $O_2$ sensors from uncommon dye/polymer combinations or from 'hard' polymers which are not so suitable for traditional techniques.

One can therefore see multiple new features and advantages of the sensors based on solvent-crazed polymers, which translate into improved analytical performance, extended range of applications and measurement tasks. Such materials display features, which are uncommon or not present in existing sensor materials (films and coatings based on bulk polymers). Properties of solvent-crazed polymer sensors appear to be quite different from those predicted for the properties of corresponding bulk polymers. Sensors produced from sheets of crazed polymers, show high reproducibility and stability of their photophysical and sensing characteristics. They allow accurate quantification of $O_2$ in the gaseous and liquid samples by measuring sensor luminescent characteristics such as fluorescence intensity, lifetime or phase signals.

The invention and corresponding materials are particularly suited for applications where the sensors need to be produced on a mass scale, cheaply and reproducibly, and/or integrated in a large number of samples. Examples of such applications include sensors for disposable use, e.g. in packaged food, chemical, pharmaceutical, medical and biotechnology products, semiconductor electronics, in environmental monitoring and industrial process control. For example, the PtOEPK-HDPE based $O_2$ sensors facilitate incorporation in various types of samples and packaging materials by simple heat-sealing process.

The invention also provides the process of fabrication of optical $O_2$ sensors, which includes the selection of appropriate oxygen-sensitive dye and polymer matrix which provide the desired sensitivity and selectivity for the analyte, optionally formation of the nanoporous structure within the polymer by solvent crazing process, impregnation of this nanoporpous structure with the dye, and, if required, post-treatment of the polymer to modify the structure by healing the nanopores. As described above, different stages of this process can be conducted separately, or combined in one process which includes solvent-crazing, impregnation and post-treatment. The preferred methods of impregnation with the dye are those which provide uniform, homogeneous distribution of the dye in its monomeric form within the polymer, and optimal sensitivity and selectivity for the analyte. The latter can be fine-tuned by post-treatment which involves healing of the porous structure. This fabrication technology also provides a number of improvements over prior art.

In addition, the nanoporous structure and large volume capacity of the $O_2$ sensors of invention facilitate their use as transducers. Thus, after solvent-crazing and impregnation with indicator dye, the $O_2$ sensors can be coated with an oxygen-dependent enzyme to produce a biosensors for important metabolites. Thus, the surface of solvent-crazed $O_2$ sensor can be coated by applying enzyme solution on its surface and crosslinking the enzyme with glutaraldehyde. After such immobilisation, biosensors showing high specific activity and stability were produced. Using this approach, biosensors for glucose (glucose oxidase), lactate (lactate oxidase) and other important substrates of oxygen-dependent enzymes and metabolites were produced.

Furthermore, the design and fabrication of indicator based sensors illustrated above with examples of $O_2$ sensors can also be applied to sensors for other physical and chemical parameters, particularly temperature, $CO_2$, pH. For specialists in the area it is clear that many of the features described for $O_2$ sensors based on solvent-crazed polymers will be retained in sensors for the other parameters.

The following non-limiting examples illustrate the fabrication, properties and applications of such sensors.

Example 1

Impregnation of Solvent-Crazed Polymers with $O_2$-Sensitive Dyes and Fabrication of $O_2$ Sensors Using hand-operating clamps, strips of HDPE film with gage dimensions of 50×20 mm and thickness of 60 microns were stretched in hexane along the direction of melt-extrusion by a tensile strain of 175%, and allowed to dry under a stream of air while remaining stretched. A solution of PtOEPK dye in hexane (1.0 mg/ml) was applied dropwise on the surface of hexane-crazed HDPE matrix with a pipette and allowed to dry under fixed dimensions in air for 10 min. The resulting polymers stained with the dye (thickness of ~40 microns) produced the phosphorescent material which can be used for sensing of O2.

Using hand-operating clamps, strips of HDPE with gage dimensions of 15×100 mm and thickness of 25 microns were stretched in hexane along the direction of melt-extrusion by a tensile strain of 120% and allowed to dry under a stream of air. This solvent-crazed HDPE matrix was submerged in a solution of PtOEPK dye in hexane (0.5 mg/ml) while maintaining fixed dimensions in the clamps, taken out and allowed to dry in air for 10 min. After that the polymer was additionally stretched by 50% along the direction of initial stretching. Thus, O2 sensor elements with healed nanostructure were produced.

Similarly, strips of HDPE with gage dimensions of 50×20 mm and thickness of 60 microns were stretched in hexane along the direction of melt-extrusion by a tensile strain of 175% and allowed to dry under a stream of air. A solution of PtOEPK in hexane (1 mg/ml) was applied on the surface of crazed HDPE matrix and allowed to dry in air for 10 min. After that the samples were released from the clamps and allowed to relax at 100° C. in free hanging state. Finally they were rinsed with hexane to remove the excess of dye from the surface. Thus, O2 sensor elements with healed nanostructure were produced.

Strips of standard (molten) polypropylene film with gage dimensions of 15×100 mm and thickness of 25 microns were stretched in hexane along the direction of melt-extrusion by a tensile strain of 60% and allowed to dry under a stream of air. The solvent-crazed PP matrix was submerged in a solution of PtOEPK dye in hexane (0.5 mg/ml) while maintaining fixed dimensions in the clamps, taken out and allowed to dry in air for 10 min. After that the polymer was annealed at 120° C. for 2 hours to produce O2 sensor elements with healed nano-structure.

A strip of PVC with gage dimensions of 50×20 mm and thickness of 80 microns was stretched in isopropanol by a tensile strain of 75% and allowed to dry under a stream of air. PtOEPK solution in hexane (0.2 mg/ml) was applied on the surface of wet-crazed PVC matrix and allowed to dry in air for 10 min. Sensor strips were then rinsed with hexane to produce the phosphorescent material.

In a similar way, sensors were produced using other O2-sensitive dyes, namely Pd-octaethylporphine-ketone Pt-tetrakis(pentafluorophenyl)porphine, Pt-octaethylporphine, and Ru(II)-diphenylphenantroline perchlorate, Pd-chlorin e6, Pt(II)-mesomethylpheophorbid and Pt(II)-mesopyropheophorbid.

Example 2

Preparation of $O_2$ Sensors in a Continuous Process

A computer-controlled set-up was constructed which serves to orient polymer films and fibers in a precise and controlled way and to provide continuous stretching and solvent crazing of polymer tape. It involved feed rolls, a guide roll, a solvent bath, take-off rolls, and a winder. A general sketch is shown in FIG. 1 in which 1 is the roll of the initial polymer film (may be a non-oriented or slightly oriented film, 2 indicates the film guiding rolls, 3 indicates the film feeding module with two guiding rolls 3a, a feeding roll rotating at a pre-set speed 3b, and a film aligning roll 3c, 4 indicates a crazing bath with active solvent and a set of four guiding rolls 4a, 5 indicates a receiver module with two guiding rolls 5a, a receiving roll rotating at pre-set speed 5b, and a guiding roll for folding the polymer tape 5c, and 6 indicates a module for winding the processed film into rolls. Polymer film 1 having width 10-50 mm, thickness 20-100 microns was first directed by the film aligning roll 3c to the feed rolls 3b rotating at a given speed. The polymer film then passed the guide roll 3a, passes through the bath 4 containing crazing-promoting solvent via the guide rolls 4a, and passes onto the take-off rolls 5a, 5b, 5c. The difference in rotation speed of the feed and take-off rolls controls the stretching ratio of the film. Stretched polymer articles containing solvent-crazed nanoporous structures are collected on a winder. Using this set-up, production of the nanoporous structure in polymers such as HDPE and PP is performed. Impregnation of the polymer matrix with PtOEPK or other indicator dye is conducted on this equipment, using the dye dissolved in crazing-promoting solvent in the bath 4. Alternatively, after its initial stretching in solvent-crazing bath, the polymer film can be impregnated with the indicator dye by passing it through another bath containing solution of the dye in appropriate solvent or by applying dye solution on the surface of the polymer film (spraying, printing or spotting). This set-up also allows incorporation of a heating unit, which provides healing of the nanoporous structure of the polymer film after its solvent-crazing and impregnation with the dye. Using this prototype equipment and sensor fabrication process, a continuous sensor tape was produced using the following parameters:

Polymers type—amorphous HDPE, PP, PET.
Tape physical dimensions: thickness—25 um, width—15 mm, length—100 m.
Tape feeding speed—5 m/min
Crazing and impregnation solution: 0.5 mg/ml of PtOEPK in hexane
Bath size and solution volume: 10×10×5 cm, 20 ml
Stretching during crazing—175%
Healing process—drying in relaxed state.

Example 3

Properties of $O_2$ Sensors Based on Solvent-Crazed Polymers

O2 sensors based solvent-crazed HDPE and PP polymers, produced according to the procedures described in Examples 1,2, were investigated for their photophysical and sensing properties. For all the polymers, relatively high degree of impregnation with the dyes was achieved. Thus, the PtOEPK-HDPE sensors produced from a 25 micron thick tape according to Example 2 showed absorbance values typically ranging between 0.02-0.2 at 586 nm (absorption maximum for PtOEPK), after their heat-treatment and sealing of the nanopores. Phosphorescent signals were comparable to those of traditional sensors.

Figure 2:
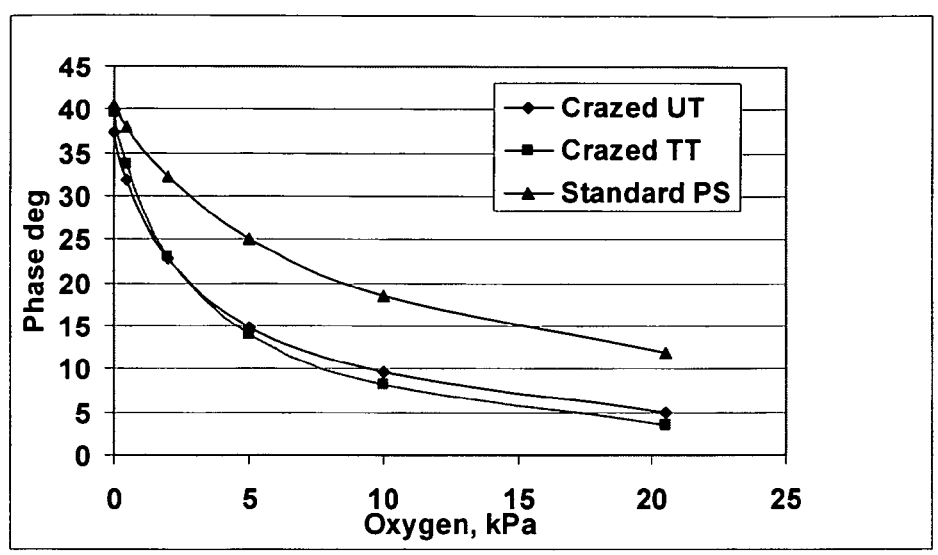
FIG. 2. Oxygen calibrations for the standard PtOEPK-polystyrene and solvent-crazed PtOEPK-HDPE sensors, measured on the phase detector (working frequency—2.6 kHz) in the gas phase at 22° C.

Phosphorescence signals obtained from the sensors were high enough to measure O2 in the gaseous and aqueous samples by phase-fluorometry. Measurements performed with a bench-top phase-fluorometric detector described in (Papkovsky D B et al—Analytical Letters, 2000, v.33(9), 1755-1777) produced the following calibrations for the untreated (open nanopores) and heat-treated (healed pores) HDPE sensors (FIG. 2). One can see that the response of both types of sensors to $O_2$ is higher than for the conventional PtOEPK-polystyrene thin film sensors.

A more detailed analysis of sensor response to $O_2$ showed high linearity of Stern-Volmer calibrations for the sensors based on solvent-crazed polymers (FIG. 3), even though their quenching and signal changes were rather large. In contrast, PtOEPK-PS sensors showed non-linear calibrations. This data confirms that solvent-crazed polymer matrices such as HDPE and PP produce very homogeneous O2-sensitive materials.

Figure 3A:
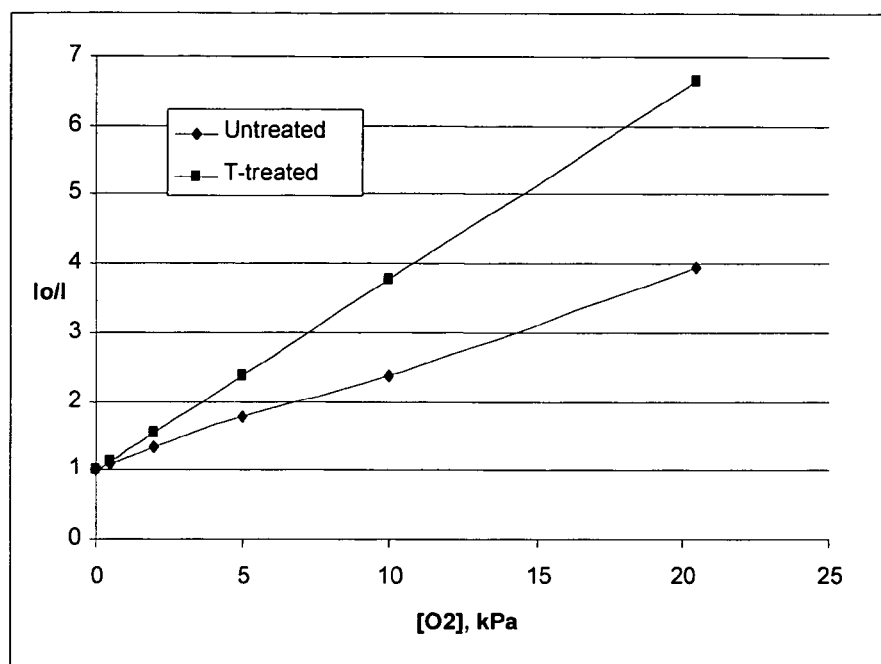
FIG. 3. Oxygen calibrations (A) and phosphorescence intensity signals (B) for the untreated and heat-treated (40 min incubation at 110° C.) solvent-crazed PtOEPK-HDPE sensors. Measurements were made on the phosphorescence phase detector at working frequency 2.6 kHz, at 22° C.
Figure 3B:
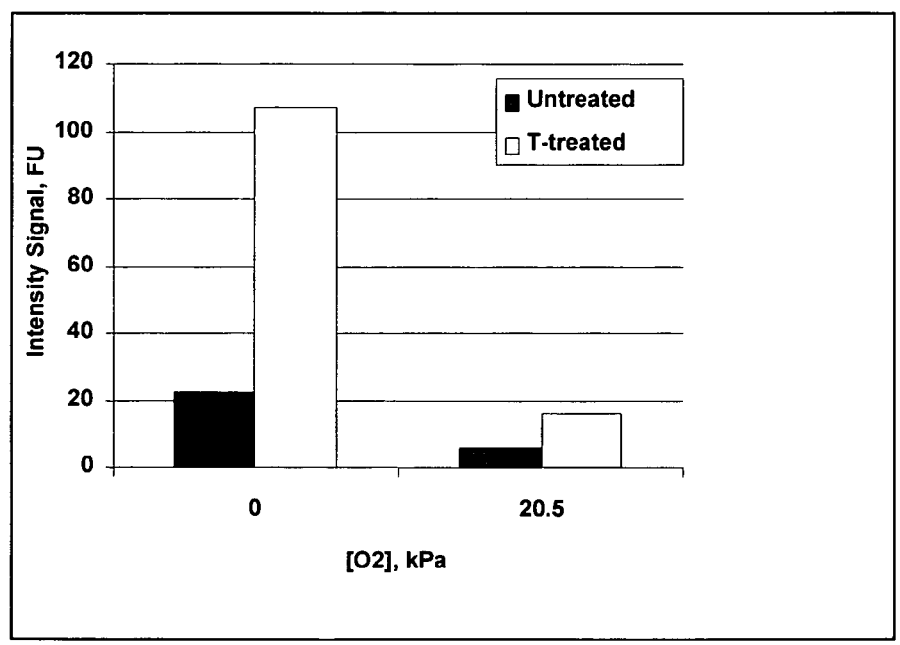

Furthermore, heat treatment of solvent-crazed O2 sensors which heals their nanoporous structure resulted in a significant increase of intensity signals obtainable from such sensors (2-4 fold) and also higher response to O2 (FIG. 3). These sensors are brighter and more sensitive to O2 than the untreated ones. Reproducibility of signals from individual sensors from the same batch was also improved after post-treatment and the linearity and stability of calibrations were preserved. In such sensors the dye molecules are shielded from other chemical specie which can potentially interfere. Temperature dependence of calibrations for the solvent-crazed O2 sensors were also more favourable compared to the respective sensors produced by conventional technology.

O2 sensors based on solvent-crazed HDPE and PP were also made using PdOEPK dye which has longer emission lifetime and higher quenchability by O2. As expected, these sensors showed a significantly higher sensitivity than similar sensors based on PtOEPK. This is due to the longer emission lifetime of PdOEPK. Impregnation by solvent crazing process with PtOEPK dye of other polymers having lower gas permeability characteristics than PP and HDPE was also undertaken. Thus, PVC and Teflon produced O2 sensors with practically no or largely reduced sensitivity to O2, respectively. All this is in general agreement with the theory of quenched-fluorescence O2 sensing.

Example 4

Sensor Incorporation and Use in Packaging Materials

The PtOEPK-HDPE sensors with healed pores produced as described in Example 2 in the form of a tape, were used to incorporate them in various samples comprising different packaging materials and also to make individual O2 sensors. Thus, pieces of sensor tape were attached to the inner side of packaging films (transparent sheets of polymer film laminates with a gas-barrier outer film e.g. polyamide, polyester and a heat-sealable inner film PE/PP) by means of a simple heat-sealing device, and then separated from the tape with a cutter. These sensors incorporated in packaging materials were then measured in a contactless fashion (i.e. from the gas-barrier side of the laminate) under ambient air with the above phosphorescence phase detector. They all gave similar phase signals which corresponded to ambient O2 levels. These packaging materials integrated with the PtOEPK-HDPE sensors were used to package a batch of food products under modified atmosphere (low O2, high N2). After packaging the actual levels of O2 in the headspace of these packs (defined by the composition of the modified atmosphere) were tested by measuring the phase signals from the sensors and converting these signals into O2 concentration using calibration function generated for this batch of sensors. When simulating package damage by opening the packs, the sensors were seen to give fast and easily measurable response to changes in O2 concentration. The sensors were therefore efficient for the contactless and non-destructive monitoring of O2 in a sealed vessel, such as food or pharmaceutical packages packed under protective atmosphere. They allow easy integration in the packaging process thus facilitating monitoring of residual O2 levels and quality control of individual packages.

Example 5

Sensors for Other Parameters Based on Solvent-Crazed Polymers

PVC film was stretched by 30% in heptane, dried and annealed to stabilize the formed open-pore structure. This structure was impregnated with PtOEPK or PdOEPK dye by applying a solution of the dye in hexane. The polymer was then heat-treated to heal the pores. The resulting material showed strong phosphorescence, practically no sensitivity to oxygen, but at the same time pronounced, reversible changes of its phosphorescence characteristics: a decrease in lifetime and intensity with temperature in the range from 0 to 50° C. Thus, such polymeric materials (and also PET based) can be used as a temperature sensors.

The invention is not limited to the embodiment hereinbefore described which may be varied in both construction, detail and process step without departing from the spirit of the invention.

The invention claimed is:

1. A process for producing an optochemical sensor suitable for sensing $O_2$, said process comprising the steps of:
   solvent-crazing an amorphous or semi-crystalline polymeric material selected from high density polyethylene, polypropylene, and polyolefins to form a multiplicity of nanopores having an average pore size of less than 50 nm; and impregnating the nanopores with molecules of a photoluminescent $O_2$ sensitive dye having an emission lifetime in the microsecond range, wherein the resulting optochemical sensor shows a characteristic optical response to $O_2$ by altering the parameters of its photoluminescence.

2. The process of claim 1, wherein the solvent-crazing step and the impregnating step are carried out in a single step, and the photoluminescent $O_2$ sensitive dye is incorporated into the solvent employed in the solvent-crazing step.

3. The process of claim 1, wherein solvent crazing comprises drawing the polymeric material by a factor of at least 1%.

4. The process of claim 1, further comprising healing the pores of the polymeric material impregnated with the photoluminescent $O_2$ sensitive dye.

5. The process of claim 4, wherein healing the pores comprises drying the solvent crazed polymeric material.

6. The process of claim 5, further comprising stretching or heat treating the relaxed polymeric material.

7. The process of claim 1, wherein providing a polymeric material comprises providing a polymeric material having an elongated form and a thickness of from 5 to 500 μm.

8. An optochemical sensor suitable for sensing $O_2$, said sensor being manufactured by the process of claim 1.

9. The process of claim 1, wherein the photoluminescent $O_2$ sensitive dye is Pt(II)-octaethylporphine-ketone or Pd(II) octaethylporphine-ketone.

10. The process of claim 1, wherein the photoluminescent $O_2$ sensitive dye is selected from the group consisting of Pt(II) and Pd(II) complexes of tetrakis(pentafluorophenyl) porphine, octaethylporphine, tetraphenylporphine, or benzoporphyrin; and long-decay fluorescent complexes of Ru(II)polypyridyl, cyclometalated iridium(III), or osmium(II).

* * * * *